United States Patent [19]

Schulbach

[11] Patent Number: 4,769,512
[45] Date of Patent: Sep. 6, 1988

[54] BEAN PLANT HAVING LOW POD DETACHMENT FORCE

[75] Inventor: Roy Schulbach, Salem, Oreg.

[73] Assignee: NPI Seed, Inc., Salem, Oreg.

[21] Appl. No.: 911,377

[22] Filed: Sep. 24, 1986

[51] Int. Cl.[4] .............................................. A01H 5/00
[52] U.S. Cl. .................................... 800/1; 47/DIG. 1
[58] Field of Search .................. 800/1; 47/58, DIG. 1

[56] References Cited

U.S. PATENT DOCUMENTS 3,861,079  1/1975  Patterson .
4,351,130  9/1982  Rutger et al. .
4,377,921  3/1983  Mehra-Palta et al. .
4,378,655  4/1983  Johnson .
4,581,847  4/1986  Hibberd et al. .

OTHER PUBLICATIONS

Bassett, "Evaluation of Snap Bean Cultivars for Pod Detachment Force," HortScience, vol. 8(5):411 (1973).
Bassett, "Inheritance of Pod Detachment Force in Snap Beans," Phaseolus vulgaris L.," HortScience, vol. 11(5):471-72 (1976).
Showalter, "Detachment Force for Harvesting Snap Beans," Florida State Horticultural Society, 115-17 (1969).
Showalter, "Detachment Characteristics of Snap Bean Pods and Pedicels," Florida State Horticultural Society, 248-52 (1970).

Primary Examiner—Robert E. Bagwill
Attorney, Agent, or Firm—Klarquist, Sparkman, Campbell, Leigh & Whinston

[57] ABSTRACT

A novel plant genotype characterized by the expression of a low pod detachment force in Phaseolus. The seed which carries the genetic code for this characteristic is capable of germinating into a plant having a mean pod detachment force (PDF) of about 0.51 kg or less when pods are at market maturity size. The plant is further characterized by an erect shape having pods clustered high in the bush, and easy detachability of the pedicel from the stem at nodes. The low PDF characteristic can be used to develop new low PDF varieties through hybridization with high PDF lines of Phaseolus.

20 Claims, 1 Drawing Sheet

U.S. Patent    Sep. 6, 1988    4,769,512
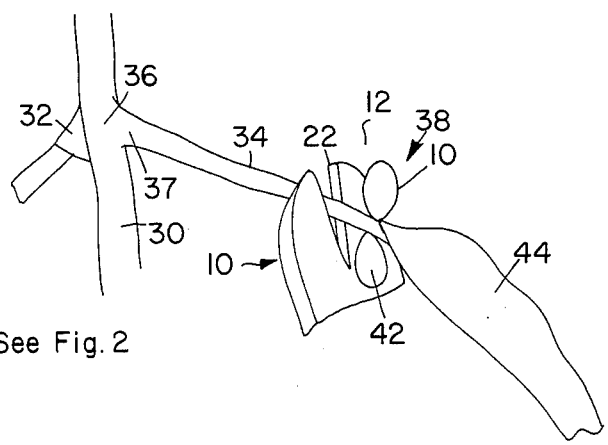
FIG. 2
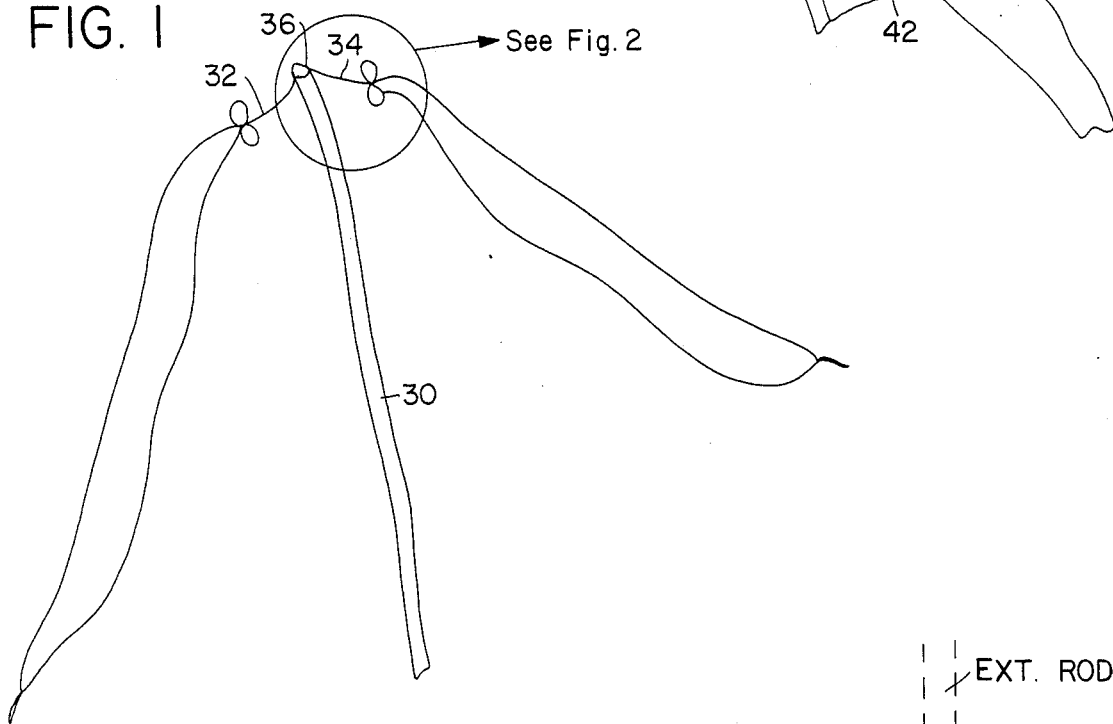
FIG. 1
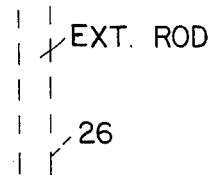
FIG. 3
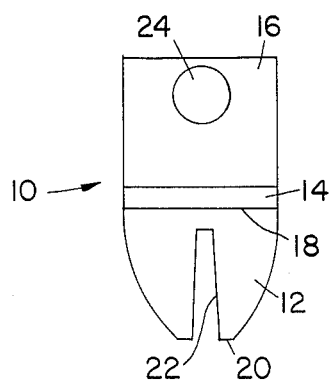
FIG. 4
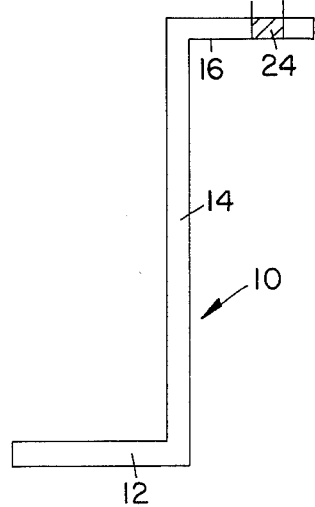

BEAN PLANT HAVING LOW POD DETACHMENT FORCE

CROSS REFERENCE TO RELATED APPLICATIONS

Priority is claimed from the disclosure in co-pending plant variety protection application Ser. Nos. 8500079 and 8500080, both filed Mar. 6, 1985.

BACKGROUND OF THE INVENTION

1. Field of the Invention

This invention concerns novel plant genotypes for Phaseolus, and more particularly concerns bean seeds and plants germinated therefrom which produce easily harvestable pods.

2. General Discussion of the Background

Beans are an important staple food item for human consumption. The broad beans (*Vicia Faba*), soy beans (*Glycine Max*), and a few other types have long been known in Europe, but the choice food beans of the modern world are the large-seeded species of Phaseolus. This species includes lima beans, scarlet runner beans, string beans, shell beans, white beans, black beans, pea beans, black-eyed beans, and kidney beans. The most widely cultivated of the beans is *Phaseolus vulgaris*, which includes green, string, snap or wax beans, as well as many types of dry beans, such as kidney, pea, pinto, Great Northern, marrow, yellow-eye, and others.

The commercial importance of these beans has made it necessary to find methods of harvesting them mechanically from the bushes on which they grow. Mechanical harvesters, such as the Chisholm-Ryder Multiple Density Harvester, have been developed for this purpose. The Chisholm-Ryder harvester lifts prostrate beans from the ground to an upright position using a set of two horizontal brushes driven hydraulically at a speed of about 175 RPM. The upright beans are then stripped from the bush by a series of metal or rubber picking fingers arranged horizontally on a reel. As the beans are stripped from the bush, the leaves and stems are also removed. All of this material is then carried bhy a conveyor to a device called the stripper, which detaches the stems and leaves from the picked beans. After passing through the stripper, the beans, stems and leaves are conveyed through a set of two cleaning fans which, at a speed of 1500 RPM, separate the lighter weight stems and leaves from the pods. This lighter weight material ("trash") is blown out of the machine by exhaust fans, while the pods are conveyed to a storage hopper. It would be desirable to eliminate or reduce the extra equipment and processing steps required for removing stems and leaves from the pods.

In addition to mingling bean pods with unwanted debris, the high speed stripping action of the picking reel breaks many pods. It is therefore also necessary to hand inspect products and discard broken pods to obtain an end product of uniform quality. These extra steps of removing debris and inspecting pods increase the complexity and cost of bean processing. A bean bush having pods that can be mechanically harvested without such problems would be commercially advantageous.

It is therefore an object of this invention to provide a bean plant having characteristics which allow pods to be mechanically harvested while reducing the amounts of stems and leaves which ar pulled from the bush.

It is another object of the invention to provide such a bean plant having pods that can be harvested with a lower speed picking reel than in the prior art.

Yet another object of the invention is to provide such a plant having pods that can be harvested with reduced abrasive action against the plant.

Even yet another object is to provide a bean plant having pods that can be harvested with fewer broken pods to provide a higher quality product for processing.

Still another object is to provide a bean plant which can be harvested with significant processing plant savings by reducing the need for line inspection and mechanical cleaning equipment.

Finally, it is an object of the invention to provide a bean plant which produces decreased amounts of trash during mechanical harvesting.

These and other objects of the invention will become apparent from the following detailed description.

SUMMARY OF THE INVENTION

This invention is directed to novel plant genotypes, and in particular novel genotypes of Phaseolus, and especially beans of the species *Phaseolus vulgaris*. As exemplary embodiments, two green bean plants (*Phaseolus vulgaris* leguminosae) are described herein, both of which have a mean pod detachment force (PDF) of about 0.51 kilograms or less, preferably about 0.38 or less, and most preferably about 0.28 or less, when the bean pod is at market maturity size. The plant is capable of producing seed which germinates into a plant having a similar mean PDF of about 0.51 kilograms or less. The low PDF of these novel plants permits bean pods to be easily mechanically harvested from bean bushes. In comparision to the prior art, the reel speed of the harvester can be reduced without a reduction in the number of pods obtained. Lower reel speeds remove fewer leaves, stems and clusters from the bush, thereby reducing the amount of debris that must be separated from the pods during processing.

In *Phaseolus vulgaris* leguminosae, low PDF is most significant in pods having sieve size 1–4 (pod width 4.76 mm–9.53 mm). The low PDF characteristic in the exemplary embodiment is attenuated, although still present, above sieve size 4 (for example, in sieve sizes 5 and 6). Low PDF is present in sieve size 4 pods, which is the preferred market size for these beans. Even within sieve size 4 there is a variation in PDF, with the most pronounced low PDF values being obtained in beans from the lower end of the range of width included in sieve size 4. Lower PDFs would be obtained, for example, in beans having a pod width of 8.34 to about 9.0 mm, and would usually be lowest in pods 8.34 mm wide.

The exemplary embodiments, in addition to having the low PDF described above, are characterized by an unusually high incidence of three pods at some nodes of some low PDF plants. The plant is also characteristically erect with pods clustered on pedicels high in the plant, and the point of detachment from the stem usually occurs where the pedicel attaches to the stem.

This invention also includes the seeds which are produced by such low PDF plants, as well as any plants produced or germinated therefrom, or hybrid plants into which the low PDF characteristic is introduced, as well as their progeny and seeds.

The following detailed description presents two specific examples of the invention. These particular embodiments relate to low PDF bean plants having genotypes which allow the bean pods to be easily mechanically harvested at low reel speeds with minimal damage to the plant and minimal collection of extraneous material. The following detailed description is intended to be exemplary and not limiting in scope.

BRIEF DESCRIPTION OF THE DRAWINGS

FIG. 1 is a schematic view of a stem of a low PDF bean plant having two pods attached to pedicels at a single node of the stem.

FIG. 2 is an enlarged fragmentary view of one of the pedicels and pods of the bean plant shown in FIG. 1, the positioning of a pedicel-engaging portion of a strain gauge on the pedicel being shown.

FIG. 3 is a side view of the pedicel-engaging portion of the strain gauge used to measure PDF in the present invention.

FIG. 4 is a top view of the portion of the strain gauge shown in FIG. 3.

FIG. 5 is a photograph of a group of low PDF bean plants which are disclosed embodiments in accordance with the present invention.

FIG. 6 is another photograph of low PDF bean plants similar to those shown in FIG. 5.

DETAILED DESCRIPTION OF PREFERRED EMBODIMENTS

The exemplary embodiments of this invention relate to seeds which are capable of germinating into a garden bean plant (*Phaseolus vulgaris* leguminosae). The two varieties of Phaseolus which are described in detail are designated AgS1 and AgS2. AgS1 is the subject of pending plant variety protection application No. 8500079, filed Mar. 6, 1985, while AgS2 is the subject of pending plant variety protection application No. 8500080, filed Mar. 6, 1985. The information contained in each of these plant variety applications is incorporated herein by reference.

AgS1

AgS1 originated as an individual plant selected from a population of crosses involving diverse bush Blue Lake types of beans. The parentage is undocumented, but is known to include Oregon State University and other Oregon-adapted parents, such as OSU 58R from Oregon State University.

AgS1 most closely resembles, while still differing from, a plant type such as bush Blue Lake 290, or Epoch. AgS1 is characterized by extremely easy removal of pods from the vine, especially when the pods are at optimum maturity sizes (sieve sizes 1–4, especially sieve sizes 3–4).

AgS1 is a garden-type bean which develops edible pods about 71 days after planting. Dry seeds are produced 101 days after planting. The average height of the plant is 50 cm, and it has a 50 cm spread with three to four primary branches near its base. Its branching habit is compact and the main stalk is stout.

The plant is a high bush form, having pods positioned near the top of the plant. The plant leaves are wrinkled, glossy and dark green in color, as dark or darker than bush Blue Lake 290. The size of the leaves is medium, between the size of Earliwax and Tender Crop beans. It produces white flowers, and it takes about 50 days after planting for 50% of the flowers to bloom. Its fresh pods have a dark green exterior color, as dark or darker than bush Blue Lake 290 beans. The percentage sieve size distribution at optimum maturity for non-flat pods is shown below in the following table:

| % Sieve Size Distribution for AgS1 at Optimum Maturity for Non-Flat Pods | | | | | |
|---|---|---|---|---|---|
| Sieve size: | 1 | 2 | 3 | 4 | 5 | 6 |
| Percentage: | 1% | 7% | 7% | 35% | 45% | 5% |
| Approximate Dimensions of AgS1 for Sieve Size 3–6 | | | | | |
| 3 sieve | = | 13 cm long | 8 mm wide | 8 mm thick |
| 4 sieve | = | 14 cm long | 9 mm wide | 9 mm thick |
| 5 sieve | = | 16 cm long | 9 mm wide | 9 mm thick |
| 6 sieve | = | 17 cm long | 10 mm wide | 10 mm thick |

Fresh pods have a round cross-sectional pod shape without a crease back. The spur is slightly curved and the pod has no constrictions. Pod flesh is medium in color. Spur length is about 17 mm, and there are about seven seeds per pod. The surface of the pod is smooth, and no suture string is present. The pods are ideally suited for machine harvesting, and have a flavor similar to strong Blue Lake (pole FM 1).

The seed coat color is a shiny, monochromatic white. Seed shape is elliptical from a hilum view, round in cross section, and oval to oblong in side view. The ends of the seed are round. The weight of the seeds is about 29 grams per 100 seeds.

Anthocyanin is absent from the flowers, stems, pods, seeds and leaves. AgS1 is known to be susceptible to bean yellow mosaic virus, but tolerant to halo blight and resistant to bean common mosaic virus $BV_1$.

AgS2

AgS2 originated as an individual plant selected from a population of crosses involving diverse bush Blue Lake type beans. The parentage is undocumented, but, like AgS1, is known to include Oregon State University and other Oregon adapted parents, such as OSU 58R from Oregon State University.

AgS2 most closely resembles a plant type such as bush Blue Lake 290 or Epoch. It is characterized by an extremely low PDF and other characteristics set forth below.

AgS2 is a garden-type bean, which produces edible pods 75 days after planting, and dry seeds 105 days after planting. It requires 1040 heat units to produce edible pods and 1480 heat units to produce dry seeds.

The AgS2 plant is 55 cm high, and has a 50 cm spread with three to four primary branches near its base. The main stalk is brittle and stout. The plant has a high bush form with pods positioned high in the bush. Its leaves are glossy, wrinkled and of medium size (intermediate the sizes of Earliwax and Tender Crop). The color of the leaves is dark green, which is defined as dark or darker than bush Blue Lake 290. Flowers produced by the plant are white, and it takes about 53 days after planting for 50 per cent of the flowers to bloom.

The fresh pods are characterized by a dark green exterior color, which is as dark or darker than bush Blue Lake 290. Percentage sieve size distribution at optimum maturity for non-flat pods is illustrated in the following table:

| % Sieve Size Distribution for AgS2 at Optimum Maturity for Non-Flat Pods | | | | | | |
|---|---|---|---|---|---|---|
| Sieve size: | 1 | 2 | 3 | 4 | 5 | 6 |
| Percentage: | 1% | 7% | 7% | 35% | 45% | 5% |
| Approximate Dimensions of AgS2 for Sieve Size 3–6 | | | | | | |
| 3 sieve = | 13 cm. long | | 7 mm. wide | | 7 mm. thick | |
| 4 sieve = | 15 cm. long | | 9 mm. wide | | 8 mm. thick | |
| 5 sieve = | 16 cm. long | | 10 mm. wide | | 9 mm. thick | |
| 6 sieve = | 17 cm. long | | 11 mm. wide | | 9 mm. thick | |

Fresh pods have a round cross sectional shape with no creased backs. The spur is slightly curved and the pod has no constrictions. Pod flesh is medium in color, and spur length is about 16 mm. Pods characteristically have seven seeds per pod, and the pod has a smooth surface and no suture string. The pod flavor is similar to the flavor of strong Blue Lake (pole FM1).

Seed coat color is a shiny, monochromatic white. The seed is eliptical in hilum view, round in cross section, and slightly reniform in side view. The seeds have round ends, and weigh about 29 grams per 100 seeds.

Anthocyanin is absent from the flowers, stems, pods, seeds and leaves.

AgS2 is known to be tolerant to halo blight and resistant to bean common mosaic virus $BV_1$, but susceptible to bean yellow mosaic virus.

Pod Characteristics of AgS1 and AgS2 Which Enhance Mechanical Harvesting

The low PDF characteristics of AgS1 and AgS2 greatly minimize mechanical harvest loss, reduce cullage, and improve processing plant efficiency. In addition to the easily removed pods, the plants have several other characteristics which contribute to a reduction in trash and broken beans during mechanical harvesting. The bean plant is erect, with pods fairly clustered and positioned relatively high in the bush. Vines of the bush are less interweaved than in many prior bushes, thereby allowing the beans to more readily break away during mechanical harvesting.

The beans also have several qualities which provide outstanding canning characteristics. Undesirable fiber content in the can is reduced because of the bean's excellent pod symmetry and absence of creased back and flattened pods. Pod color, texture, firmness and smoothness all compare favorably with prior varieties. Interlocular cavitation is very low, which enhances slicing properties, especially in the french-cut bean style. AgS1 and AgS2 have a medium pod length which allows them to be cut more quickly than the longer pods of other beans, and more efficiently than shorter bean pods which produce more waste ends during slicing.

Method of Determining PDF

PDF values were obtained using an AccuForce Cadet Force Gauge from Ametek-Hunter Spring Division of Hatfield, Pa. 19440. The force gauge was modified by adding an attachment for hooking pods. The attachment 10, shown in FIGS. 2-4, includes a piece of strap metal bent at right angles to form a pod pulling portion 12, intermediate flat portion 14, and rod attachment portion 16. Pulling portion 12 is wedge-shaped, and narrows from a wide base 18 to a relatively narrow tip portion 20. A slot 22 extends through pulling portion 12 from its tip portion 20 toward its base 18. The width of slot 22 decreases from 4 mm. at tip 20 to about 1 mm. at its terminal end adjacent base 18. The widest portion of slot 22 is wider than the pedicel of a green bean plant, and the slot 22 narrows to a width which can firmly engage opposing sides of a pedicel adjacent the calyx.

Attachment portion 16 of strain gauge 10 defines an internally threaded hole 24, which receives an extension rod 26, which is connected to the AccuForce strain gauge described above but not shown in the drawings.

FIGS. 1 and 2 show a Phaseolus bean plant having a stem 30 with two pedicels 32 and 34 extending outwardly from a node 36 of stem 30. The enlarged view of pedicel 34 in FIG. 2 shows that pedicel 34 terminates at a calyx 38, which includes upper sepal 40 and lower sepal 42. A bean pod 44 extends outwardly and slightly downwardly from calyx 38.

PDF was measured using attachment 10 by orienting slot 22 vertically and placing it over pedicel 34 between calyx 38 and node 36, but adjacent calyx 38 as shown in FIG. 2. The widest portion of slot 22 was placed around pedicel 34 first, and attachment 10 was then moved upwardly until a narrower portion of slot 22 engaged opposing sides of pedicel 34. This narrower portion was sufficiently small to prevent calyx 38 from pulling through slot 22.

After attachment 10 was placed around pedicel 34 in the manner shown in FIG. 2, attachment 10 was moved vertically upwardly by extension rod 26 attached to the strain gauge (not shown). The force gauge measured vertical forces until the pedicel 34 broke from stem 30 at node 36. The force gauge then maintained the peak reading, which was recorded.

The point of detachment in AgS1 and AgS2 was consistently at the point of attachment 37 between pedicel 34 and main stem 30. Prior varieties detach at either end of the pedicel, and are much less easily characterized with respect to their point of detachment.

PDF was measured only for pods having a sieve size four.

Using the foregoing method of measuring PDF, the following data was obtained:

TABLE 1

Mean and range of pod detachment force (kg) measurements in Phaseolus at several different locations in 1985 and 1986.

| Location and Year | GENOTYPE | | | | | |
|---|---|---|---|---|---|---|
| Homestead, Florida | GP82-160 | Savor | Blazer | Strike | Triumph | AgS2 |
| | | | | N = 90 | | |
| 1985 Mean | 1.27 | 1.13 | 1.13 | 1.09 | 1.00 | .41 |
| Range | .54–2.27 | .32–2.22 | .36–2.04 | .27–1.86 | .23–1.86 | .09–.91 |
| Salem, Oregon | Gourmand | Horizon | Stretch | BBL 290 | AgS1 | AgS2 |
| | | N = 30 | | | N = 60 | |
| 1986 Mean | 1.11 | 1.23 | 1.06 | 1.57 | .27 | .28 |
| Range | .60–1.53 | 60–1.79 | .45–1.58 | .83–2.25 | .02–.70 | .05–.95 |
| Pratum, Oregon | BBL 290 | | AgS1 | | | AgS2 |

TABLE 1-continued

Mean and range of pod detachment force (kg) measurements in
Phaseolus at several different locations in 1985 and 1986.

| Location and Year | GENOTYPE | | |
|---|---|---|---|
| | | N = 60 | |
| 1986 Mean | 1.29 | .38 | .48 |
| Range | .61–2.09 | .05–.81 | .15–1.08 |
| Salem, Oregon | Slenderette | Harvester | AgS1 |
| | | N = 30 | |
| 1986 Mean | .82 | .97 | .53 |
| Range | .40–1.61 | .43–1.58 | .10–1.66 |

The data in Table 1 illustrates that no other bean genotype expresses a mean PDF of 0.51 kg or less at sieve size 4. All of the measured PDF's are well above this value. The reported mean PDF of AgS1 in the Salem, Oreg. 1986 comparison to Slenderette and Harvester shows a mean PDF of 0.53 for AgS1. This PDF is slightyl higher than 0.51 since AgS1 pods that were tested were slightly more mature than market maturity.

A mean PDF value of 0.51 kg for the present invention was chosen after a statistical analysis of the data which was the basis for Table 1. This analysis indicated that a low PDF genotype, in accordance with the present invention, would be characterized by about a 0.51 kg or less PDF at sieve size 4. It is possible, of course to perform plant selections through breeding in such a way that mean PDF will exceed 0.51 kg while still being low enough to retain the benefits of this invention.

The following Tables 2–5 illustrate the probability of a statistical significance between AgS1, AgS2 and non-low PDF varieties.

TABLE 2

Probability for a statistical significance between PDF means of AgS1, AgS2 and non-low PDF varieties, Salem, Oregon, 1986.

| | Gourmand | Horizon | Stretch | BBL 290 |
|---|---|---|---|---|
| AgS1 | .001 | .001 | .001 | .001 |
| AgS2 | .001 | .001 | .001 | .001 |

TABLE 3

Probability for a statistical significance between PDF means of AgS1 and AgS2 and BBL 290, Pratum, Oregon, 1986.

| | AgS1 | AgS2 |
|---|---|---|
| BBL 290 | .001 | .001 |

TABLE 4

Probability for a statistical significance between PDF means of AgS1 and non-low PDF varieties, Salem, Oregon, 1986.

| | Slenderette | Harvester |
|---|---|---|
| AgS1 | .001 | .001 |

TABLE 5

Probability for a statistical significance between means of AgS2 and non-low PDF varieties, Homestead, Florida, 1985.

| | GP82-160 | Savor | Blazer | Strike | Triumph |
|---|---|---|---|---|---|
| AgS1 | .001 | .001 | .001 | .001 | .001 |

The data in Tables 2–5 illustrate the high likelihood of a statistically significant difference between AgS1, AgS2 and the compared varieties. A statistical significance of 0.05 or less indicates a high probability that the strains are different.

TABLE 6

PDF for multiple sieve sizes in AgS2.

| Sieve Size | No. Pods (n) | PDF X (kg.) | Pod Width (mm) |
|---|---|---|---|
| 1 | 58 | .39 | 4.76–5.76 |
| 2 | 58 | .43 | 5.76–7.34 |
| 3 | 49 | .43 | 7.34–8.34 |
| 4 | 46 | .51 | 8.34–9.53 |
| 5 | 61 | .56 | 9.53–10.72 |
| 6 | 27 | .74 | 10.72 & Greater |
| 6 + 2[1] | 4 | .95 | |

[1]This identifies pods measured two days after sieve 6 was reached.

Table 6 shows that the low PDF characteristic of the present invention is attenuated as pod sieve size increases. The importance of this attenuation is diminished by the fact that market demand decreases for beans above sieve size 4.

TABLE 7

Seed fresh weight as a percentage of total pod weight for AgS1 and AgS2.

| Sieve Size | AgS1 % | AgS2 % |
|---|---|---|
| 1 | 3.8 | 3.7 |
| 2 | 3.8 | 4.1 |
| 3 | 4.3 | 4.2 |
| 4 | 5.0 | 4.9 |
| 5 | 6.0 | 6.0 |
| 6 | 6.9 | 6.8 |

TABLE 8

Comparison of AgS1 and AgS2 with non-low PDF varieties for machine harvest cullage, Salem, Oregon, 1985.

| Variety | Foreign Material (%) | Broken Pods and Mechanical Damage (%) | Total Cullage (%) |
|---|---|---|---|
| AgS1 | 1.3 | 1.8 | 65 |
| Check[1] | 2.6 | 2.2 | 100 |
| AgS2 | 2.3 | 2.3 | 74 |
| Check[2] | 3.6 | 2.6 | 100 |
| AgS2 | 3.0 | .9 | 63 |
| Check[2] | 3.6 | 2.6 | 100 |

[1]Check consisted of both OSU 1604 and OSU 91
[2]Check was BBL 290.

Data for Table 8 were obtained by machine harvesting AgS1, AgS2 and the compared varieties OSU 1604, OSU 91 and BBL 290. Percentage amounts of foreign material, broken pods and total cullage were reduced in AgS1 and AgS2 because of the reduced PDF.

DEFINITION OF MARKET MATURITY

Even if bean seeds are planted in a field at the same time, the individual pods on the plants will reach a market maturity at different times. Mechanical harvesters remove all the beans, regardless of their size. To deal with this situation, bean breeders and processors have developed definitions of "market maturity" which recognize that each crop at a given maturity will yield pods of a predominant sieve size intermingled with a substantially constant ratio of pods at other sizes. Since these ratios differ from one type of bean to another, the following definitions of "market maturity" are given for various recognized classes of edible pod beans.

1. Large sieve bush green beans: sieve size 4 wherein the machine harvest yields about 50% sieve sizes 1-4.
2. Small sieve bush green beans: sieve size 2 wherein the machine harvest yields about 90% sieve sizes 1-3.
3. Large sieve bush yellow beans: sieve size 4 wherein the machine harvest yields about 50% sieve sizes 1-4.
4. Medium size pod of Romano or Italian beans (also known as large flat-podded bush beans): suture to suture distance of about 10-20 mm, wherein the sizes of the beans are distributed across this range.
5. Medium sized pod of small flat-podded bush beans: thickness (suture to suture) of about 5-10 mm, wherein the thicknesses of the beans are distributed across this range.
6. Large sieve tall-vine green beans (also known as pole beans): sieve size 4 (no optimum machine harvest stated because these beans are continuously hand picked).
7. Romano pole beans (medium sized pod of large flat-podded tall-vine beans): thickness of about 10-20 mm.

Market maturity is defined in this manner to avoid a skewing of mean PDF values that could occur if market maturity were only defined as a given sieve size. If, for example, large sieve green beans were defined only as sieve size 4, it would be possible to measure PDFs of only very mature sieve 4 beans. Such measurements would skew the mean PDF value to an artifically high level since mean PDF increases with increasing pod sizes, even within a single sieve size.

The list of seven types of beans for which a definition of "market maturity" is given is thought to be comprehensive. For any types of beans that have been omitted from this list, the definitions of the term "market maturity" will be known to those skilled in the art.

Method of Hybridization

The low PDF trait of the present invention can be introduced into many different varieties of beans by hybridization. This technique can be used to make low PDF large sieve bush green beans (having an optimum harvest about 50% sieve size 1-4), as well as small sieve bush green beans (having an optimum harvest about 90% sieve size 1-3). Other beans into which the trait can be introduced include, without limitation: large sieve bush yellow beans; large flat-podded bush beans (also called Romano or Italian beans) having a suture to suture distance of about 10-20 mm; smaller flat-podded bush beans such as the Bountiful variety having a suture to suture distance of about 5-10 mm; large sieve tall-vine beans (also called pole beans); and large flat-podded tall vine beans.

Hybridization is accomplished by hand crossing AgS1 or AgS2 with plants having genotypes for higher PDF. No selection is made in the first filial ($F_1$) generation. Seed for $F_1$ comes from a single hand pollinated pod containing 1 to 7 seeds. Seed harvested from the $F_1$ plant(s) derived from a single pod is used to plant the $F_2$ generation in a row plot. Beginning with the $F_2$ generation, one or more individual plants are selected based on low PDF and superior plant and pod horticultural characteristics. While PDF can be quantitatively measured, it is sometimes more expedient to subjectively test for PDF by hand detachment, since large numbers of crosses and plants must be tested in the scope of a comprehensive breeding program. The selections of $F_2$ will be planted in $F_3$ rows, where single plant selections will again be made. This cycle continues until the breeder has attained a desired combination of traits in a plant with low PDF. This cycle is usually completed by $F_5$ or $F_6$ if low PDF is detected in the $F_2$. There are times, however, where too few $F_2$ plants or other factors cause abandonment of some $F_2$ plots as a result of insufficiently low PDF levels.

One important reason for continuing selections through $F_5$ or $F_6$ is to achieve stabilization of low PDF and other traits. By $F_6$, nearly 100% homozygosity is achieved and the trait is stable.

Theory Concerning Inheritance

Without being bound by theory, the inventor believes that the low PDF trait of AgS1 and AgS2 is controlled by two or more nonallelic genes. Support for this belief comes from an evaluation of inheritance patterns in $F_1$ and $F_2$ generations of high PDF×low PDF crosses. When PDF values of the $F_2$ generation are plotted, the resulting curve is bell shaped. Such a curve is characteristic of traits controlled by multiple genes.

For example, AgS1 was crossed with AS40-07, a higher PDF breeding line. Thirty parental plants, 31 $F_1$ plants and 290 $F_2$ plants were evaluated for PDF using an AccuForce Cadet force gauge. A plot of PDF values for the $F_2$ plants versus number of plants observed for that value resulted in a normal curve, i.e., a bell-shaped curve in which the number of plants at each increasing level of PDF increased until reaching a peak, and then the number of plants decreased similarly at higher PDF values. A plot of the PDF values for the $F_1$ plants revealed no dominance effect from the higher PDF parent.

Basset proposed in *HortScience*, Vol. 11 (5), October 1976, 471-472, that PDF in Phaseolus is controlled by a minimum of two dominant genes. To test this hypothesis, AgS1 was crossed with Idelight (mean PDF about 1.1 kg), which was the lowest PDF bean Basset tested. PDF in the resulting $F_1$ was not measured to be as low as AgS1, as would be expected if genes of both beans were identical for PDF inheritance.

The foregoing observations suggest, without being conclusive, that AgS1 and AgS2 have at least three genes with primarily additive effects which control PDF and yield mean PDF's of 0.51 or less at market maturity.

Seed Deposit

A collection of seeds, identified as "AgS1", as described herein, has been deposited with American Type Culture Collection, Rockville, Md., and has been assigned Accession No. 40263.

A collection of seeds, identified as "AgS2", as described herein, has been deposited with American Type Culture Collection and assigned Accession No. 40262.

The present invention is not to be limited in scope by the seeds deposited, since the deposited embodiments are intended as mere illustrations of the invention, and any seeds or plants which are functionally equivalent are within the scope of this invention. Indeed, various modifications of the invention, in addition to those shown and described herein will become apparent to those skilled in the art from the foregoing description. Such modifications are intended to fall within the scope of the appended claims.

I claim:

1. A seed capable of germinating into a *Phaseolus vulgaris* plant which produces bean pods with a mean bean pod detachment force of about 0.51 kg or less when said bean pods are market maturity size.

2. The bean seed of claim 1 wherein said plant is capable of producing seed which is capable of germinating into a plant having a mean bean pod detachment force of about 0.51 kg or less when said pod is market maturity size.

3. A seed capable of germinating into a *Phaseolus vulgaris* plant which produces pods, said plant being capable of expressing genetic coding for cell development at a point of pod detachment which yields a mean pod detachment force of about 0.51 kg or less when said pods are sieve size 4.

4. The seed of claim 3 wherein said plant is capable of transmitting said genetic coding to its progeny.

5. The bean seed of claim 3 wherein said bean pod is about 8.34 mm wide at market maturity.

6. A bean seed of the variety deposited with ATCC and assigned Accession No. 40263.

7. A plant which germinates from green bean seed deposited with ATCC and assigned Accession No. 40263.

8. A seed obtained from said plant of claim 7 or its progeny.

9. A hybrid Phaseolus plant obtained by crossing a plant which germinates from a seed of the variety deposited with ATCC and assigned Accession No. 40263, with another Phaseolus plant.

10. A bean seed of the variety deposited with ATCC and assigned Accession No. 40262.

11. A plant which germinates from bean seed of the variety deposited with ATCC and assigned Accession No. 40262.

12. A seed obtained from said plant of claim 11 or its progeny.

13. A hybrid Phaseolus plant obtained by crossing a plant which germinates from a seed of the variety deposited with ATCC and assigned Accession No. 40262, with another Phaseolus plant.

14. A hybrid *Phaseolus vulgaris* bean plant capable of producing seed which is capable of germinating into a plant producing bean pods having a mean bean pod detachment force of about 0.51 kg or less when said bean pods are market maturity size.

15. A seed obtained from said hybrid plant of claim 14 or its progeny.

16. A method for producing Phaseolus bean seed, comprising crossing a first *Phaseolus vulgaris* bean line capable of producing seed which is capable of germinating into a *Phaseolus vulgaris* bean plant which produces pods having a mean pod detachment force of about 0.51 kg or less when said pods are at market maturity, with another Phaseolus bean line.

17. A seed capable of germinating into a *Phaseolus vulgaris* plant having:
a stem with pedicels originating at nodes, and pods growing from said pedicels, said plant being characterized by preferential detachment of said pods and pedicels from said plant at said node with a mean pod detachment force of about 0.51 kg or less when said pod is market maturity size.

18. The seed of claim 17 wherein said plant germinated from said seed is erect with pods clustered high on said plant.

19. A seed capable of germinating into a *Phaseolus vulgaris* leguminosae plant having:
a stem;
an erect shape with pods clustered high on said stem; and
a plurality of pedicels attached to said stem at nodes, and a plurality of bean pods depending from said pedicels;
said bean pods and pedicels being detachable from said stem by a mean bean pod means detachment force of about 0.51 kg or less when said bean pods are market maturity size.

20. The seed of claim 19 wherein said pedicel of a plant germinated from said seed is characterized by a cellular weakness at said node such that said pedicel consistently detaches from said stem at said node when said pods are removed from said plant.

* * * * *

UNITED STATES PATENT AND TRADEMARK OFFICE
CERTIFICATE OF CORRECTION

PATENT NO. : 4,769,512
DATED : September 6, 1988
INVENTOR(S) : ROY SCHULBACH

It is certified that error appears in the above-identified patent and that said Letters Patent is hereby corrected as shown below:

In the Specification:

Column 1, line 44, "bhy" should be --by--.
Column 2, line 2, "ar" should be --are--.
Column 6, Table 1, "60-1.79" should be --.60-1.79--.
Column 7, Table 5, "AgS1" should be --AgS2--.

In the Claims:

Claim 19, line 37, after "pods", delete --means--.

Signed and Sealed this

Twenty-eighth Day of February, 1989

Attest:

DONALD J. QUIGG

Attesting Officer

Commissioner of Patents and Trademarks